United States Patent [19]
Dukes et al.

[11] Patent Number: 4,716,363
[45] Date of Patent: Dec. 29, 1987

[54] EXPONENTIAL DECAY TIME CONSTANT MEASUREMENT USING FREQUENCY OF OFFSET PHASE-LOCKED LOOP: SYSTEM AND METHOD

[75] Inventors: John N. Dukes, Los Altos Hills; William F. Carlsen, Jr., Mountain View; Richard J. Pittaro, San Carlos, all of Calif.

[73] Assignee: Hewlett-Packard Company, Palo Alto, Calif.

[21] Appl. No.: 47,818

[22] Filed: May 8, 1987

[51] Int. Cl.⁴ ............................................. G01R 23/16
[52] U.S. Cl. ................................ 324/77 R; 324/78 R; 331/25
[58] Field of Search ................. 324/77 R, 77 A, 77 B, 324/77 C, 77 CS, 77 D, 77 H, 78 R, 78 D, 78 Z, 79 R, 79 D, 83 R, 83 A, 83 D, 57 R; 375/84; 455/183; 331/25

[56] References Cited

U.S. PATENT DOCUMENTS 3,939,405  2/1976  Mutziger ......................... 324/57 R
4,109,283  8/1978  Rast ................................. 455/183
4,670,887  6/1987  Heatherington ...................... 375/84

Primary Examiner—Michael J. Tokar
Attorney, Agent, or Firm—Clifton L. Anderson; John A. Frazzini

[57] ABSTRACT

Oxygen determination based on luminescence quenching of fluorescent dye is effected by using the frequency output of an offset-phase locked loop to calculate the time constant for the exponential decay of fluorescence. An offset phase angle between a periodic stimulus signal used to excite the dye and a response signal based on fluorescence detection is predetermined to optimize signal-to-noise ratio for a wide range of time constants. An offset-phase locked loop is used to vary the frequency of a periodic stimulus signal until the predetermined phase relationship is established. Where the stimulus and response signals are substantially sinusoidal, the offset phase angle is ideally about 49.3°, although substantially optimal performance is achieved using a more conveniently generated 45°. The 45° angle offset can also be used with a square-wave stimulus signal.

18 Claims, 2 Drawing Figures

EXPONENTIAL DECAY TIME CONSTANT MEASUREMENT USING FREQUENCY OF OFFSET PHASE-LOCKED LOOP: SYSTEM AND METHOD

BACKGROUND OF THE INVENTION

The present invention relates to measurement, and, more particularly, to a system and method for measuring exponential decay time constants and parameters derivable therefrom. While the present invention has many applications, it has particular application to the measurement of oxygen concentration, for example, in blood, based on luminescence quenching.

Oxygen concentration in various solutions, e.g., blood, can be measured by determining a fluorescence decay time constant. A fluorescent dye, protected as appropriate, can be dissolved in a sample solution. Fluorescence is initiated by stimulating the dissolved dye with light of an appropriate wavelength. In a case where the stimulus is abruptly terminated, the fluorescence does not end instantaneously. Rather, the fluorescence decays according to an exponential decay function.

In such a dyed sample solution, fluorescence is quenched by the presence of oxygen so that the intensity and duration of the fluorescence are decreased as a function of oxygen concentration. Theoretically, oxygen concentration could be measured as a function of either intensity or duration. However, intensity is difficult to work with as it varies with many system variables such as temperature, stimulus intensity, optomechanical coupling, fiber bending losses, etc.

Since fluorescent decay can be characterized exponentially, the exponential time constant, $\tau$, of such fluorescent decay can be used as an amplitude independent measure of oxygen concentration. The time constant for a sample can be determined directly by stimulating and then abruptly terminating stimulation of a dyed sample, and then finding a time interval over which intensity decreases by a factor of $1/e$, about 63%. Similarly, the percent change over a fixed time interval can be used to determine the time constant. Due to the pervasive presence of noise, such direct methods do not afford very high precision unless averaging is performed over many measurements. Thus, a periodic, rather than a one-shot, stimulus is usually preferred.

For example, in a pulse method, a sample is stimulated with a pulse train to yield a periodic response signal. The average delay of the response with respect to the stimulus is used as a measure of oxygen concentration. One major disadvantage of the pulse method is the difficulty of producing sharply defined stimulus pulses. Generally available light sources yield pulses several nanoseconds in duration, which is often already a substantial fraction of fluorescent lifetimes.

While it is possible to use iterative convolution to parcel out the effect of the extended pulse duration from the exponential decay, this requires very carefully controlled pulse shapes. The mathematics involved in iterative convolution are even more complicated in cases where the decays overlap due to a high-frequency stimulus signal. Another solution is to use lasers with picosecond pulse width, but such lasers are not widely available due to cost and technical considerations.

A phase-shift method can be used which avoids some of the disadvantages of the pulse method. In a typical application of the phase-shift method, the sample is stimulated with sinusoidally modulated light. The output in such a case is the convolution of the stimulus sine wave and the system exponential function, which is also a sine wave but with a shifted phase. Thus, the time constant can still be determined indirectly from the phase of the response signal relative to the stimulus signal. Phase can be readily determined by using a variety of phase detectors.

The phase-shift method has several advantages. Short, even sub-nanosecond, time constants can be easily measured. Data acquisition is relatively rapid, which is generally convenient and critical where the parameter of interest can change quickly.

Another important advantage of the phase-shift method is that it is readily adapted to more complex sample analysis where multiple time constants can be superimposed on each other. In theory, it is possible to record directly the individual time constant of each fluorescent source in a mixture using the phase-shift method.

There remain two significant disadvantages to the phase-shift approach. In the first place, phase can be difficult to measure with great precision. Phase detectors can be sensitive to amplitude effects, and thus distorted readings are difficult to avoid.

In the second place, the sensitivity of systems implementing the phase-shift method generally vary as a function of phase shift. In other words, outside a narrow range of phases, the signal-to-noise ratio is below the maximum achievable.

In some systems, provision is made for multiple frequencies for the stimulus signal. This multiplies the range of sample characteristics that can be detected using optimal phase ranges. However, the selection of the alternate frequencies is an inconvenience to the user, perhaps requiring a succession of useless measurements to be made before the desired one is achieved. In the meantime, validity erodes as sample parameters can change. Futhermore, this approach still does not provide continuous optimal sensitivity.

This limitation in sensitivity can be very significant in systems which, because of limited stimulus intensity or sample responsiveness, the desired signal is of comparable intensity to noise. In these cases it may not be possible to obtain a valid measurement outside of the maximum sensitivity range of the instrument. Thus, a phase-shift system would not be able to provide valid measurements over a continuous extended range.

Given the disadvantages of available methods as applied to oxygen measurements as well as a broad range of applications involving exponential decay, what is needed is an improved system and method for determining exponential decay time constants. The system should be convenient to use and provide optimal sensitivity over an extended and continuous measurement range. In addition, the measurement approach should be susceptible to convenient and precise readout.

SUMMARY OF THE INVENTION

In accordance with the present invention, exponential decay time constants are determined as a function of a stimulus signal frequency forced by an offset-phase locked loop to yield a stimulus-response phase angle which provides substantially optimal sensitivity. A system implementing the above approach can include a sample interface, an offset-phase locked loop, a frequency counter and a calculator for deriving a parameter value of interest from the output of the frequency counter.

An offset-phase locked loop can include a phase detector, a variable frequency generator, and a phase shifter. These components can be designed, arranged and combined in a variety of ways. The magnitude of the offset phase angle is preferably between 40° and 60°, inclusive. Where the stimulus signal is sinusoidal, an offset phase of about 49.3° can be used to optimize sensitivity. However, a more conveniently generated 45° angle can achieve substantially optimal sensitivity.

By selecting a predetermined phase, substantially maximal sensitivity can be maintained while measuring a wide range of time constants. Frequency can be conveniently and precisely measured using a frequency counter, without the interference from amplitude effects to which phase detectors are exposed. While the present invention employs a phase detector, it is operating at 90° phase differential where its output is zero independent of input signal amplitudes. Thus, it is operating at the point least subject to amplitude errors.

In accordance with the foregoing, an improved system and method for measuring exponential decay time constants provides convenient and precise readout and optimal sensitivity over a wide range of time constants. Other features and advantages of the present invention are apparent in the context of the description below with reference to the following drawings.

DESCRIPTION OF THE PREFERRED EMBODIMENTS

Figure 1:
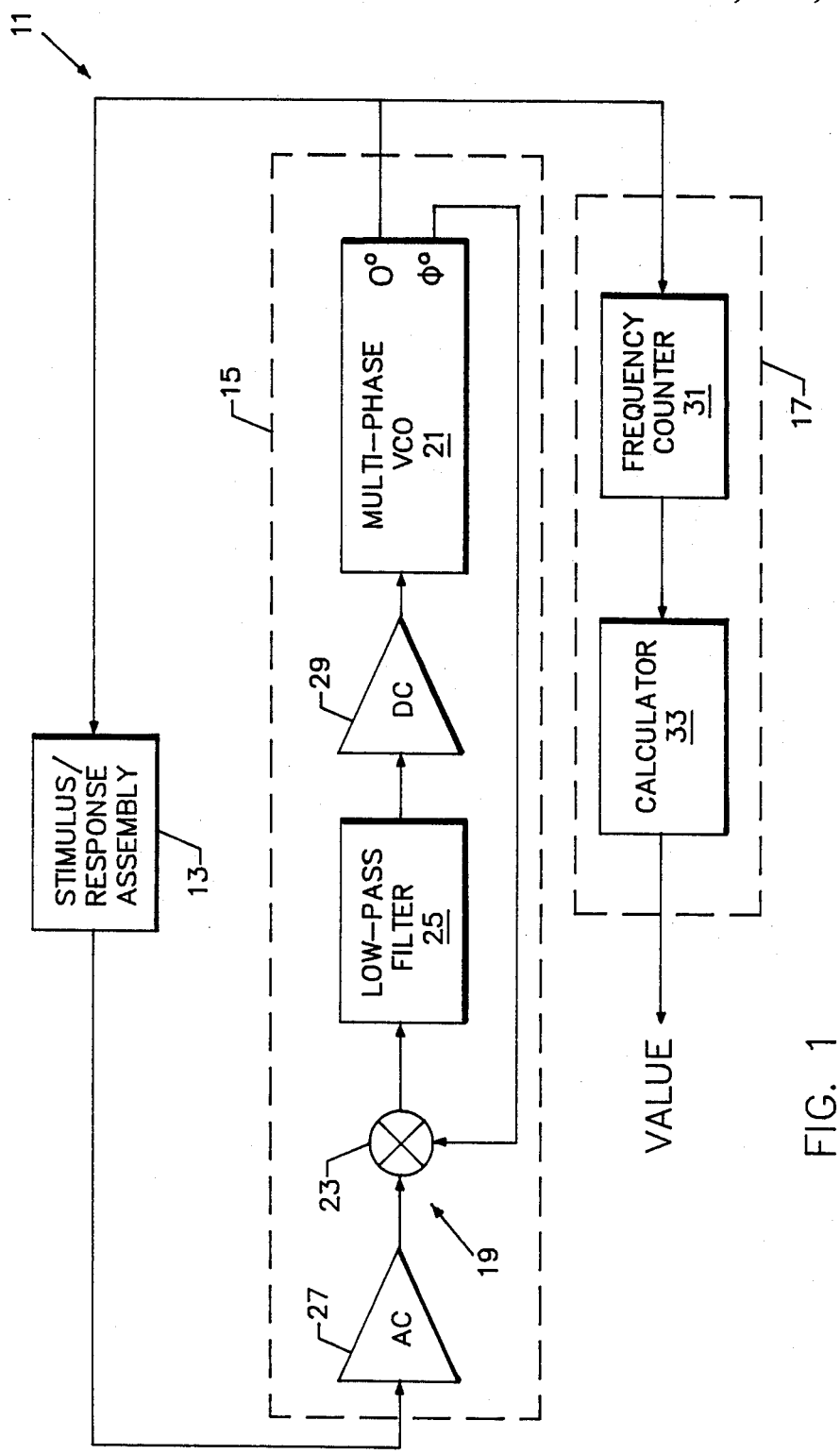
FIG. 1 is a block diagram of a system for measuring an exponential decay time constant in accordance with the present invention.

A measurement system 11 includes a stimulus/response assembly 13, an offset-phase locked loop 15 and an output processor 17. The stimulus/response assembly 13 is designed to hold a sample to be measured, and to illuminate the sample according to a received stimulus signal and to convert a resulting fluorescence into a response signal. The offset-phase locked loop 15 is designed to control the frequency of a stimulus signal to force a predetermined phase angle between a response signal and the stimulus signal, the phase being selected to optimize system sensitivity. The output processor 17 is designed to determine the frequency of a stimulus signal and to convert the determined frequency into a measurement of a parameter of interest.

The main characteristic of the stimulus/response assembly 13 in the present context is its capacity to generate a periodic response signal to a periodic stimulus signal so that the relative phases of the stimulus and response signals is a function of frequency. The illustrated stimulus/response assembly 13 includes a light source arranged to illuminate a sample, and a photodiode arranged to detect fluorescence from a sample mixed with fluorescent dye. Additionally, amplifiers to strengthen signals and filters to separate stimulus and response signals are provided.

The offset-phase locked loop 15 includes a phase detector 19 and a multi-phase voltage controlled oscillator 21. The phase detector 19 includes a mixer 23 and a low pass filter 25. The mixer 23 has two inputs, one arranged to receive the response signal and the other arranged to receive a reference signal. An AC amplifier 27 is used to strengthen the response signal before mixing. The low pass filter 25 yields an essentially DC voltage level reflecting the phase difference at the mixer 23.

A DC amplifier 29 is used to establish a gain which appropriately balances stability, and acquisition speed, accuracy, and range for the offset-phase locked loop 15. The amplified DC signal is used to control the frequency of the signals generated by the multi-phase voltage controlled oscillator 21.

The multi-phase voltage controlled oscillator 21 is designed to output multiple signals sharing a common frequency while differing in phase by a predetermined amount. The illustrated multi-phase voltage controlled oscillator 21 is arranged to provide the stimulus signal to the stimulus/response assembly 13 and a reference signal to the phase detector's mixer 23.

The reference signal to the mixer 23 is phase-shifted from the stimulus signal by an angle which takes into account the 90° required for the conventional quadrature phase input to phase detectors and an optimizing offset phase angle. Depending on other system considerations, such as any phase shift introduced by the AC amplifier 27 and other system biases, an additional term can be involved in assigning the relative phases of the stimulus and reference signals. Basically, the phase of the reference signal is chosen so that the offset-phase locked loop 15 locks on the desired offset-phase angle.

In the illustrated embodiment, the stimulus signal is sinusoidal, and, correspondingly, the response signal is substantially sinusoidal. The signal-to-noise ratio for the sinusoidal response is optimal when the response signal lags the stimulus signal by about 49.3°. In the illustrated embodiment, it is more convenient to operate at integer fractions of a full cylce, so an offset angle of −45° is used to establish a near optimal sensitivity. The negative sign of the offset angle indicates that the response signal lags the stimulus signal, hereinbelow.

In a modification of the measurement system, the response signal is other than sinusoidal. A non-sinusoidal response signal can be the result of a non-sinusoidal, e.g., square wave, stimulus signal, or a result of the properties of the sample, or other stimulus/response assembly components, or a combination of the two factors. Where the response signal is non-sinusoidal, the optimal angle can deviate somewhat from −49.3°. Accordingly, the preferred offset angle can vary over a range of about −60° to −40°.

The output processor of the measurement system includes a frequency counter 31 and a calculator 33. The frequency counter 31 provides a digital representation of the frequency of the stimulus signal input thereto. The calculator 33 is arranged to receive the digital frequency count and is programmed to calculate and read out desired system output such as oxygen concentration or decay time itself.

Figure 2:
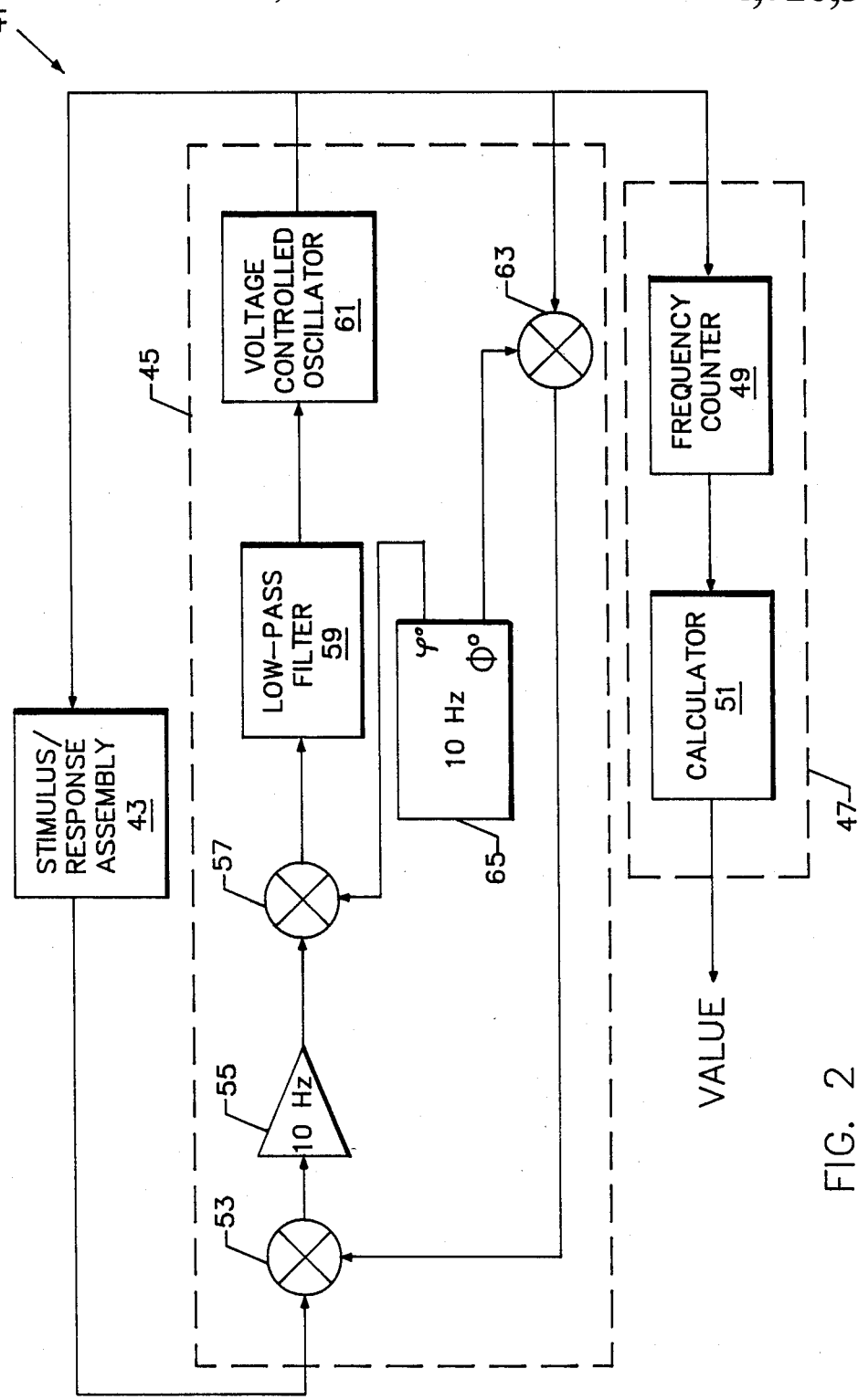
FIG. 2 is a block diagram of another system for measuring an exponential decay time constant in accordance with the present invention.

In another measurement system 41, provided for by the present invention and illustrated in FIG. 2, a measurement system comprises a stimulus/response assembly 43, an offset-phase locked loop 45 and an output processor 47. The stimulus/response assembly 43, which provides for a response signal in response to a stimulus signal provided by the offset-phase locked loop 45, and the output processor 47, which includes a frequency counter 49 and a calculator 51, are essentially the same as the corresponding components of the embodiment of FIG. 1

In the measurement system 41 of FIG. 2, the offset-phase locked loop 45 provides for the down-conversion to a fixed low-frequency signal of the response signal prior to AC amplification and phase detection. An advantage of this is that frequency related phase shifts introduced by an AC amplification do not have to be tolerated, contended with or otherwise designed around.

The down-conversion is performed at a "conversion" mixer 53 which includes a response signal input arranged to receive a response signal from the stimulus/response assembly 43 and a reference input arranged to receive a down-conversion signal. The down-conversion signal has a frequency equal to that of the response signal plus a fixed low-frequency offset, provided for as described below. The down-converted signal produced by this conversion mixer 53 is a fixed frequency signal the phase of which preserves the phase information of the response signal.

The down-converted signal is amplified by an AC amplifier 55 to provide an amplified response signal. Depending on the design of this AC amplifier 55, a phase-shift may or may not be introduced. However, since the amplified signal has a fixed frequency, phase shifts caused by frequency variations are not a concern. Also, the amplifier 55 can be of narrow bandwidth which reduces noise from cross modulation and intermodulation products generated in the phase detector.

The amplified detection signal output is then mixed with a phase-shifted reference signal at a "phase-detection" mixer 57 to yield a phase-detection signal. The frequency of the phase-shifted reference signal is the same as that of the amplified signal. The phase of the phase-shifted reference signal is chosen to be 90° from the incoming signal from the amplifier 55 so that the average voltage output of the phase-detection mixer 57 is zero volts when a desired offset phase angle is achieved between the stimulus signal and the response signal.

A low pass filter 59, which may include a DC amplifier, filters the phase-detection signal to yield a substantially DC output. In the illustrated embodiment, the bandwidth of the low pass filter is about 0.1 Hz, providing for high stability of the offset-phase locked loop 45 and considerable averaging to produce high system accuracy even if the signal response is weak and thus noisy.

The DC phase detection signal output from the low pass filter 59 is used to control a voltage controlled oscillator 61, the output of which is the periodic stimulus signal and is used for three purposes. In the first place, the stimulus signal drives the stimulus/response assembly 43. Secondly, the stimulus signal feeds the frequency counter 49 used in making the desired measurement determinations. Thirdly, the stimulus signal is input to a single-side-band generator 63.

This single-side-band generator 63 has two inputs. One is arranged to receive the stimulus signal and the other is arranged to receive an "in-phase" reference signal output from a multi-phase fixed-frequency oscillator 65. In the measurement system 41, the fixed frequency is 10 Hz. Accordingly, the output of the single-side-band generator 63 is an "in-phase" signal at the stimulus signal frequency plus the low frequency. This frequency-summed signal is the down-conversion signal used to down convert the response signal at the conversion mixer 53.

The multi-phase fixed low-frequency oscillator 65 also provides the phase-shifted reference signal to the phase-detection mixer 57. The degree of the phase shift between the phase-shifted reference signal and the in-phase reference signal includes three components. The first component is the 90° quadrature term typically used in phase detection. The second term is the desired phase offset. Since, the response signal lags the stimulus signal, this term is generally between −60° and −40°.

The third term compensates for phase shifts introduced by the offset-phase locked loop 45 prior to phase detection. For example, any phase shift imposed by the AC amplifier 55 should be reflected in the phase of the phase-shifted reference signal. As in the embodiment of FIG. 1, this term can be determined empirically. Alternatively, the AC amplifier can be designed with a particular phase shift imposed at the down-conversion frequency. In the illustrated measurement system, the AC amplifier 55 does not impose a significant phase shift at 10 Hz, so this third term can be ignored.

In the measurement system 41 of FIG. 2, the output of the voltage controlled oscillator 61 is a square wave. Thus, it is not expected that the response signal will be sinusoidal. However, due to the inherent filtering effects of the stimulus/response assembly 43, some of the higher harmonics of the stimulus signal can be lost, and the response signal accordingly can be approximate by a sinusoidal signal for purposes of determining an ideal offset-phase angle. Accordingly, a conveniently generated −45° offset phase angle provides near optimal performance in the measurement system 41.

In general, the theoretically optimal phase offset can be a function of many variables. These can include the stimulus wave shape, non-idealities in the response of the sample or the stimulus/response assembly, and influences on the response waveform itself. A sinusoidal stimulus signal can be used because it results in a predictably sinusoidal response signal, which can be analyzed straightforwardly. However, a square-wave stimulus signal can be more readily generated and can be more conveniently used for phase detection.

Influences on the response waveform can be intentionally imposed. For example, amplification and limiting can be used to provide a square waveform from a sinusoidal or other waveform. It should be noted, that while limiting can provide consistent detector sensitivity over a range of offset phases, this is at the expense of output signal-to-noise ratio below a threshold value of input signal-to-noise ratio. The effect is that the optimal phase offset for maximizing signal-to-noise ratios is, however, not significantly affected by limiting.

The preferred phase offset can deviate from the ideal offset for a number of reasons, including the convenience with which certain phase offsets can be established, as well as competing design considerations. In addition, various components can affect phase shift as a function of frequency and thus require design compromises reflected in the offset phase angle.

Furthermore, the present invention can be applied to responses which are more complex than a simple exponential decay. In some situations multiple exponential decays with different time constants can coexist; also, exponential decay can be superimposed upon other decay functions. In these situations, the present invention provides for the identification of one or more exponential terms in a response signal. For example, two or more exponential time constants can be resolved by successively changing the reference phase angles and analyzing the resultant oscillator frequency.

Many different designs can be used for the offset-phase locked loop. There are many different ways of implementing phase detection and many different types of signal generators available. There are many different approaches to coordinating phase detection and frequency generation. It is not necessary that the frequency generator be voltage controlled. A current can be used to control a current controlled device. A digital phase readout can be used to control a digitally controlled oscillator. The pairings of phase detection and stimulus signal generation functions are essentially unlimited. Furthermore, there are many possible arrangements and selections of auxiliary components such as amplifiers and filters.

The implementation of the offset phase angle can be approached in several ways. A required phase-shift function can be implemented at a multi-phase frequency generator, or integrated with a phase detector, or implemented by a dedicated phase shifter.

Furthermore, the phase shift can be fixed or selectable. A selectable phase shift can be used to permit calibration and to contribute flexibility to the incorporating instrument. This might be particularly important where provision is made for the selection of different waveforms or where some other variable affected the ideal or preferred offset-phase angle.

The output process can be implemented in a variety of ways and can include either digital or analog devices, and is likely to contain both. The frequency counter can provide a digital or analog representation of frequency. The output of the frequency counter can be programmed in a wide variety of ways, depending, in part, on the ultimate parameter being measured.

Many different stimulus/response assemblies are provided for. The stimulus source can be a light-emitting diode, a semiconductor laser, another solid-state type of laser, a gas laser or other laser, a flash-lamp, etc. Modulation can be applied by varying the intensity of the source, or by strobing the beam emitted by the source.

The coupling of the source to the sample and the sample to the detector can involve direct contact or the transmission of light through a vacuum, gas, liquid, or solid, including optical fibers. The detector can be a silicon photodiode or one of many other photo-sensitive devices. The detector output can be amplified as required.

Various fluorescent dyes can be used when measuring dissolved oxygen in blood, in organic solvents, or in aqueous samples. Such dyes can also be used for measuring oxygen levels in gas phase, e.g., mines and other industrial hazard areas, oxygen tents, etc.

Entirely different dyes can be used where the variable of interest is other than oxygen concentration. The method of the present invention can be applied to the identification of a fluorescent material, or the concentration of a fluorescent material in a sample of interest.

More generally, the present invention is applicable to measurement of many parameters over a broad range of applications across several disciplines which can be characterized by processes involving exponential decay and other functions characterized by a frequency dependent phase shift. The nature of the stimulus/response assembly, the frequency generator and incorporating offset-phase locked loop, and the output processor all can be adapted as required for the application.

Thus, the present invention provides for the foregoing embodiments and variations and modifications thereupon so that the scope of the present invention is limited only by the following claims.

What is claimed is:

1. A system for measuring a value functionally related to an exponential decay time constant, said system comprising:
   stimulus/response means including stimulus means for stimulating a sample in response to a received stimulus signal and response means for providing a response signal reflecting a response generated by said sample;
   an offset-phase locked loop including a signal generator, said generator being adapted for generating a periodic stimulus signal characterized by a frequency within a predetermined generator frequency range, said offset-phase locked loop being arranged in a feedback relation with said stimulus/response means so that said periodic stimulus signal is received by said stimulus means so as to yield a periodic response signal which is fed back to said offset-phase locked loop via said response means, said offset-phase locked loop being adapted for forcing an offset-phase angle between said periodic stimulus signal and said periodic response signal, said offset-phase angle being constant over said generator frequency range; and
   conversion means for deriving from the frequency of said stimulus signal a value related to an exponential time constant for said response signal.

2. The system of claim 1 wherein said offset-phase locked loop includes:
   a phase detector for providing a phase detection signal as a function of said periodic stimulus signal, said periodic response signal and said offset-phase angle, said phase detector having a signal input, a reference input, and an output, said signal input being arranged to receive said periodic response signal, said phase detector output being arranged for controlling said signal generator so as to determine the frequency of said periodic stimulus signal; and
   phase shifting means for providing a reference signal having the same frequency as said periodic stimulus signal and being in a predetermined phase relation therewith, said predetermined phase relation being selected so that said offset-phase angle is forced by said offset-phase locked loop.

3. The system of claim 2 wherein said phase detector includes:
   a response amplifier for providing an amplified response signal by amplifying said periodic response signal;
   a multiplier for providing a product signal by multiplying said amplified response signal and said reference signal; and
   a low pass filter for providing said phase detection signal by filtering said product signal.

4. The system of claim 3 further comprising a DC amplifier for providing an amplified phase detection signal from said phase detection signal, said amplified phase detection signal being arranged to control said signal generator.

5. The system of claim 2 wherein said phase shifting means and said signal generator collectively constitute a multi-phase controllable oscillator.

6. The system of claim 5 wherein said signal oscillator is voltage controlled so that the changes in the frequency of said periodic stimulus signal are a function of the DC voltage level of said phase detection signal.

7. The system of claim 1 wherein said conversion means includes:
- a frequency counter having an input and an output, said frequency counter being designed to provide a frequency count signal in response to a signal applied to its input, said input being arranged to receive said periodic stimulus signal; and
- a calculator arranged to receive said frequency count signal, said calculator being adapted for calculating a value related to an exponential delay time constant from the value represented by said frequency count signal.

8. The system of claim 1 wherein said offset-phase locked loop includes:
- frequency summing means for providing a frequency-shifted reference signal by mixing said stimulus signal with a fixed frequency signal, said frequency summing means having a signal input arranged to receive a stimulus signal from said signal generator, said frequency summing means also having a fixed-frequency input;
- frequency conversion means for providing a fixed frequency detection signal by mixing said response signal with said frequency-shifted reference signal;
- an amplifier for providing an amplified fixed-frequency detection signal from said fixed-frequency detection signal;
- a phase detector for providing a phase detection signal, said phase detector having a signal input and a reference input, said signal input being arranged to receive said amplified fixed-frequency detection signal from said amplifier means; and
- a multi-phase fixed frequency generator for generating first and second fixed-frequency signals with a predetermined offset-determining phase angle with respect to each other, said multi-phase fixed frequency generator providing said first fixed-frequency signal to said fixed-frequency input of said frequency summing means, said multi-phase fixed frequency generator providing said second fixed-frequency signal to said phase detector's reference input, said offset-determining phase angle being selected so that said offset-phase locked loop forces said offset phase angle between said periodic stimulus signal and said periodic response signal.

9. The system of claim 8 wherein said offset-determining phase angle is about 90° less said offset phase angle.

10. The system of claim 9 wherein said amplifier imposes a characteristic phase shift on said amplified detection signal and wherein said offset-determining phase angle is about 90° plus said characteristic phase shift less said offset-phase angle.

11. The system of claim 1 wherein the magnitude of said offset phase angle is selected from a range of angles including 40° and 60° and intermediate angles.

12. The system of claim 1 wherein the magnitude of said offset phase angle is about 45°.

13. The system of claim 1 wherein the magnitude of said offset phase angle is about 49.3°.

14. A method of measuring a parameter of a sample, said parameter being mathematically related to an exponential decay time constant characterizing a response of said sample to a stimulus, said method comprising the steps of:
- determining an offset-phase angle between a periodic stimulus signal and a resulting response signal to provide a relatively favorable signal-to-noise ratio;
- stimulating said sample with a periodic stimulus signal selected to periodically initiate exponential decay;
- detecting the resulting response signal;
- adjusting the frequency of said periodic stimulus signal to achieve said offset-phase angle between said periodic stimulus signal and said periodic response signal;
- measuring the frequency of said periodic stimulus signal; and
- calculating from said frequency the value of the parameter of interest.

15. The method of claim 14 wherein the magnitude of said offset-phase angle is selected from a range including 40° and 60° and intermediate values.

16. The method of claim 14 wherein the magnitude of said offset-phase angle is about 45°.

17. The method of claim 14 wherein said periodic stimulus signal is sinusoidal.

18. The method of claim 17 wherein the magnitude of said offset-phase angle is about 49.3°.

* * * * *